United States Patent [19]

Hellberg et al.

[11] Patent Number: 5,187,189
[45] Date of Patent: Feb. 16, 1993

[54] S-AMINOALKYL-S-ARYLSULFOXIMINES AS ANTIARRHYTHMIC AGENTS

[75] Inventors: Mark R. Hellberg, Arlington, Tex.; James R. Shanklin, Jr., Richmond, Va.

[73] Assignee: American Home Products Corporation, New York, N.Y.

[21] Appl. No.: 643,364

[22] Filed: Jan. 22, 1991

[51] Int. Cl.$^5$ ............... A61K 31/04; C07C 313/24
[52] U.S. Cl. ................... 514/608; 514/542; 514/562; 560/13; 562/430; 564/101
[58] Field of Search ............ 564/101; 560/13; 562/430; 514/608

[56]  References Cited

U.S. PATENT DOCUMENTS 4,721,809  1/1988  Busby et al. .................... 564/82

FOREIGN PATENT DOCUMENTS 1526996  10/1978  United Kingdom .
2011404  7/1979  United Kingdom .

OTHER PUBLICATIONS

J. Med Chem., 30(5), 755-758, (1987).

Primary Examiner—Jose G. Dees
Assistant Examiner—Vera C. Clarke
Attorney, Agent, or Firm—Walter Patton

[57]  ABSTRACT

This invention discloses novel sulfoximines having the formula:

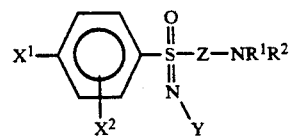

where Z is $C_1$-$C_6$ alkylene and Y is alkyl, arylalkyl, acyl, carbamoyl, sulfonyl or alkoxycarbonyl. The invention compounds are useful in the treatment of Class II arrhythmia.

5 Claims, No Drawings

S-AMINOALKYL-S-ARYLSULFOXIMINES AS ANTIARRHYTHMIC AGENTS

BACKGROUND OF THE INVENTION

1. Field of Invention

This invention relates to novel S-aminoalkyl-S-arylsulfoximines which have been found possess antiarrhythmic activity as demonstrated in an electrophysiological assay.

2. Information Disclosure Statement

The closest structurally related antiarrhythmic compounds are the benzamide (sematilide) and the benzensulfonamide (WY-48986) shown below:

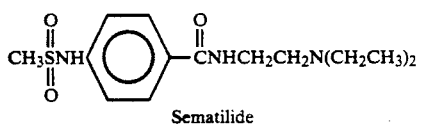

Sematilide

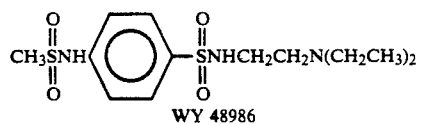

WY 48986

SUMMARY OF THE INVENTION

The antiarrhythmic compounds of the present invention are represented by Formula I

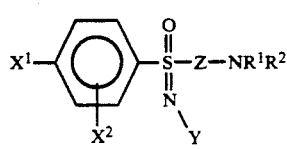

Formula I wherein:
$X^1$ is $-NO_2$, $-NH_2$, $-$halogen, $-N(R^2)-SO_2R^3$, $-NHOH$, $-CF_3$, or acetylamino;

$-NHOH$, $-CF_3$, or acetylamino;
$X^2$ is hydrogen, halogen, $C_1-C_6$ alkyl, or $-NO_2$;
Y is H, $-COR^3$, $-SO_2R^3$, $-CNR^1R^2$ (C=O), $-CR^3$ (C=O), $C_1-C_4$ alkyl or arylalkyl
Z is $C_2-C_6$ alkylene, optionally substituted by hydroxyl or methyl;
where $R^1$ and $R^2$ are H or $C_1-C_6$ alkyl, or $R^1$ and $R^2$ taken together with the interposing nitrogen forms the piperdine, piperazine, pyrrolidine or morpholine moieties, $R^3$ is $C_1-C_6$ alkyl,
and the pharmaceutically acceptable salts thereof.

In the above description of compounds represented by Formula 1, $C_1-C_6$ alkyl includes straight and branched hydrocarbons such as methyl, ethyl, propyl, butyl, pentyl, hexyl, isopropyl, sec-butyl, t-butyl, neopentyl, 2 or 3 pentyl and the like. The term $C_2-C_6$ alkylene optionally substituted by hydroxyl or methyl corresponds to

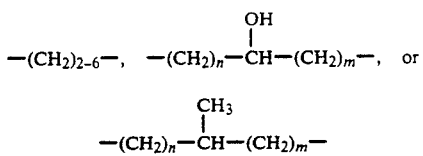

where n and m are from 0 to 5 and n+m is from 1 to 5. Arylalkyl refers to a phenyl or phenyl substituted by nitro, amino, halogen, $C_1-C_6$ alkyl or trifluoromethyl attached to a $C_1-C_4$ alkylene chain such as methyl, ethyl, propyl or butyl. The term halogen includes fluorine, chlorine, bromine and iodine. The term pharmaceutically acceptable salts refers to acid addition salts, quaternary salts, solvates, and hydrates.

Acid addition salts are those formed from the basic Formula I compounds and an inorganic or organic acid such as hydrochloric acid, sulfuric acid, phosphoric acid, fumaric acid, citric acid, maleic acid, tartaric acid, succinic acid, methane sulfonic acid, hexamic acid and the like.

The Formula I compounds are evaluated for celluar electrophysiologic effects in canine Purkinje fibers (in vitro) where the action potential duration is measured at 50% repolarization. Prolongation of the action potential duration is an indication of Class III antiarrhythmic activity.

DETAILED DESCRIPTION OF THE INVENTION

The invention compounds are prepared in several steps as outlined in the following reaction schemes.

Scheme A.
Synthesis of aryl alkyl sulfides

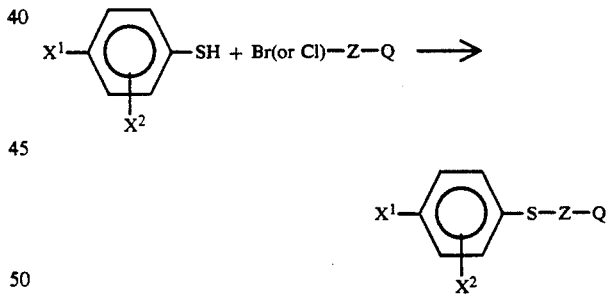

In this reaction Q is a halogen (preferably bromine or chlorine) or $NR^1R^2$ where $R^1$ and $R^2$ are alkyl groups. A suitable base such as sodium methoxide and a polar solvent such as methanol is used.

Scheme B.
Oxidation of sulfide

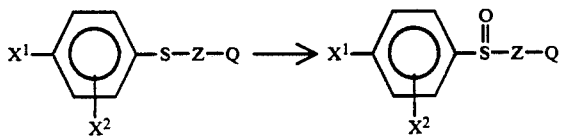

The oxidation of the sulfide to the sulfoxide is accomplished with a peracid such as m-chloroperbenzoic acid or peroxyacetic acid. Where Q is $NR^1R^2$, the oxidation of the sulfide without oxidation of the amine can be accomplished with sodium perborate in an acidic solution.

Scheme C.
Alkylation of Amine

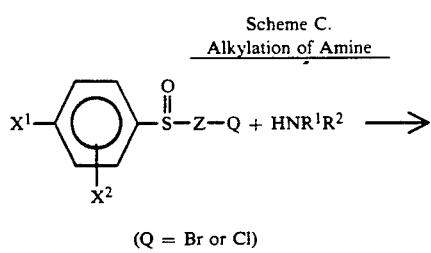

(Q = Br or Cl)

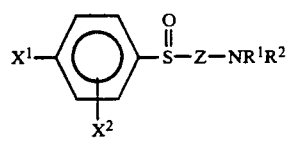

The S-aryl-S-haloalkylsulfoxide can be used to alkylate the appropriate amine using standard amine alkylating conditions to give the intermediate amines which are subsequently converted to the sulfoximines.

Scheme D.
Sulfoximine Formation

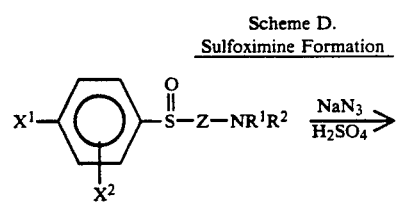

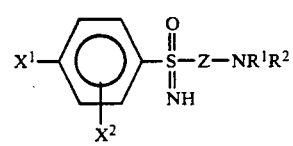

Sulfoxides are converted to the sulfoximine by reaction with hydrazoic acid.

Scheme E

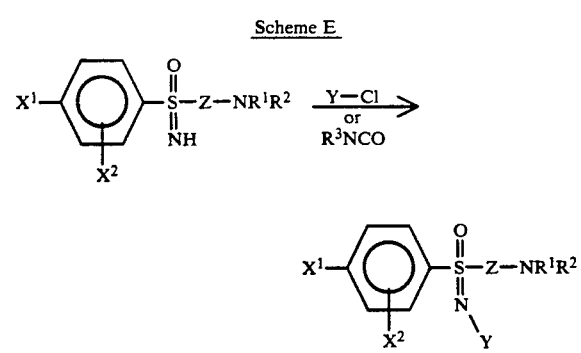

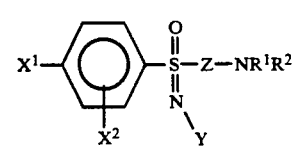

Sulfoximines formed in Scheme D are acylated or sulfonylated with an appropriate acid halide (Y-Cl) such as an alkoxycarbonyl halide, an alkylsulfonylhalide, a carbamoyl halide, an alkanoic acid halide, or an isocyanate as shown in Scheme E. Likewise, N-methyl sulfoximines can be prepared by reacting the NH sulfoximine with formaldehyde and formic acid (Eschweiler-Clarke procedure) as shown in Scheme F.

Scheme F

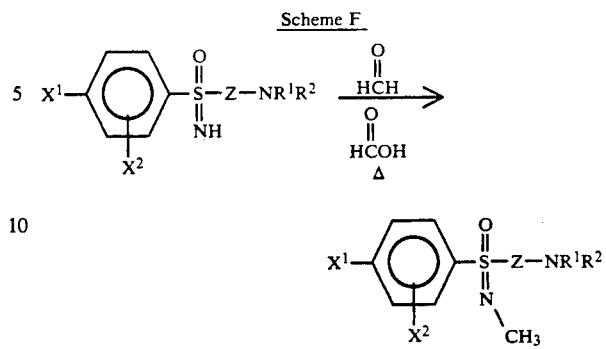

Other N-alkyl or N-arylalkyl sulfoximines of Formula I can be prepared by alkylation procedures described in Aust. J. Chem., 1986, 39, 1655-9 as illustrated in Scheme G.

Scheme G

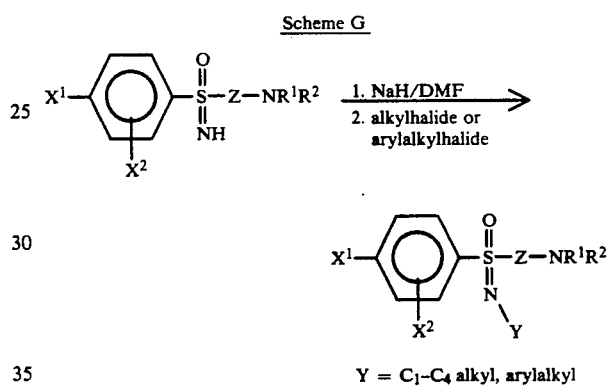

Y = $C_1$-$C_4$ alkyl, arylalkyl

The procedures given in the above reaction schemes are broadly described but it is felt that one skilled in the art of organic synthesis could practice this aspect of this invention without undue experimentation. Exact reaction conditions may vary depending on substrates, solvents, and reagents employed. The following synthetic procedures are provided as specific examples and are not to be construed as limiting to the present invention.

PREPARATION 1

1-[(3-Chloropropyl)thio]-4-nitrobenzene

4-Nitrothiophenol (80%, 25.0 g, 129 mmol) was added to a solution formed by adding sodium (5.55 g, 242 mmol) to methanol (500 mL) maintained at 0° C. After 0.5 h the reaction was warmed to ambient temperature and 1-bromo-3-chloropropane (50.7 g, 322 mmol) was added in one portion. The reaction mixture was stirred overnight and filtered. The filtrate was reduced to half volume and the solid which formed was collected by filtration. Recrystallization from methanol afforded 15.4 g (52%) of yellow solid, mp 50°-52° C.

Analysis: Calculated for $C_9H_{10}NO_2Cl$: C, 46.66; H, 4.35; N, 6.04; Found: C, 46.64; H, 4.28; N, 6.09.

PREPARATION 2

1-[(3-chloropropyl)sulfinyl]-4-nitrobenzene

A solution of m-chloroperoxybenzoic acid (80% 16.6 g, 86.3 mmol) in methylene chloride (100 mL) was added dropwise to a solution of 1-[(3-chloropropyl)thio]-4-nitrobenzene (20.0 g, 86.3 mmol) in methylene chloride (20 mL) maintained at −78° C. (dry ice/acetone bath). After 2 h the reaction was allowed to warm to ambient temperature (~1 h) and 200 mL of 10% aqueous sodium hydroxide was added. The layers were allowed to separate and the aqueous layer was extracted (100 mL) with methylene chloride. The combined organic extracts were washed (water, 100 mL), dried (MgSO$_4$) and concentrated in vacuo. A 1.0 g sample of the residue (21.2 g) was chromatographed (Chromatatron, SiO$_2$ 4000 μ, 99/1 methylene chloride:methanol) to give 0.89 g (88%) of white solid, mp 72.5°–74.5° C.

Analysis: Calculated for C$_9$H$_{10}$NO$_3$SCl: C, 43.64; H, 4.07; N, 5.66; Found: C, 43.48; H, 4.12; N, 5.63.

PREPARATION 3

N,N-Diethyl-3-[(4-nitrophenyl)sulfinyl]-1-propanamine monohydrochloride

A solution of 1-[(3-chloropropyl)sulfinyl]-4-nitrobenzene (20.0 g, 80.7 mmol) and diethylamine (14.8 g, 202 mmol) in acetonitrile was stirred for 6 h at ambient temperature. The reaction mixture was transferred to a stainless steel bomb and warmed at 80° C. for 12 h. The reaction mixture was concentrated and the residue was partitioned between 0.1N aqueous HCl (200 mL) and methylene chloride (100 mL). The layers were separated and the aqueous layer was extracted (2×100 mL) with methylene chloride. The aqueous layer was made basic with 50% aqueous sodium hydroxide and the resulting slurry was extracted (3×100 mL) with methylene chloride. The combined organic extracts were washed (100 mL H$_2$O), dried (MgSO$_4$) and concentrated in vacuo to give 10.6 g of crude product. A 1.5 g sample was dissolved in ethanol and treated with ethereal HCl. The white solid that formed was collected by filtration and dried to give 1.1 g (4%), mp 181°–182° C.

Analysis: Calculated for C$_{13}$H$_{20}$N$_2$O$_3$. S.HCl: C, 48.67; H, 6.60; N, 8.73; Found: C, 48.47; H, 6.79; N, 8.67.

PREPARATION 4

1-Bromo-4-[(2-bromoethyl)thio]benzene

Following the procedures of Preparation 1, the title compound is obtained from 4-bromothiophenol and 1,2-dibromoethane.

PREPARATION 5

1-[(5-Chloropentyl)thio]-3,4-dichlorobenzene

Following the procedures of Preparation 1, the title compound is obtained from 3,4-dichlorothiophenol and 1-bromo-5-chloropentane.

PREPARATION 6

1-[(4-Chlorobutyl)thio]-3,4-dimethylbenzene

Following the procedures of Preparation 1, the title compound is obtained from 3,4-dimethylthiophenol and 1-bromo-4-chlorobutane.

PREPARATION 7

1-[(6-Chlorohexyl)thio]-2-nitro-4-trifluoromethylbenzene

Following the procedures of Preparation 1, the title compound is prepared from 2-nitro-4-trifluoromethylthiophenol and 1-bromo-6-chlorohexane.

PREPARATION 8

4-Acetylamino-1-[(4-chlorobutyl)thio]benzene

Following the procedures of Preparation 1, the title compound is obtained from 4-acetylaminothiophenol and 1-bromo-4-chlorobutane.

PREPARATION 9

1-[(3-bromo-2-methylpropyl)thio]-4-nitrobenzene

Following the procedures of Example 1, the title compound is obtained from 4-nitrothiophenol and 1,3-dibromo-2-methylpropane.

PREPARATION 10

1-[[2-(4-morpholinyl)ethyl]thio]-4-nitrobenzene

Following the procedures of Example 1, the title compound is prepared from 4-nitrothiophenol and 4-(2-chloroethyl)morpholine.

PREPARATION 11

Following the procedures of Preparation 2 and substituting for 1-[(3-chloropropyl)thio]-4-nitrobenzene the following:
a. 4-bromo-1-[(2-bromoethyl)thio]benzene
b. 1-[(5-chloropentyl)thio]-3,4-dichlorobenzene
c. 1-[(4-chlorobutyl)thio]-3,4-dimethylbenzene
d. 1-[(6-chlorohexyl)thio]-2-nitro-4-trifluoromethylbenzene
e. 4-acetylamino-1[(4-chlorobutyl)thio]benzene
f. 1-[(3-bromo-2-methylpropyl)thio]-4-nitrobenzene
there is obtained respectively
a. 4-bromo-1-[(2-bromoethyl)sulfinyl]benzene.
b. 1-[(5-chloropentyl)sulfinyl]-3,4-dichlorobenzene.
c. 1-[(4-chlorobutyl)sulfinyl]-3,4-dimethylbenzene.
d. 1-[(6-chlorohexyl)sulfinyl]-2-nitro-4-trifluoromethylbenzene.
e. 4-acetylamino-1-[(4-chlorobutyl)sulfinyl]benzene.
f. 1-[(3-bromo-2-methylpropyl)sulfinyl]-4-nitrobenzene.

PREPARATION 12

1-[[2-(4-morpholinyl)ethyl]sulfinyl]-4-nitrobenzene

A cold (0° C.) solution of 1-[[(4-morpholinyl)ethyl]thio]-4-nitrobenzene in methanol is treated slowly with excess 30% sulfuric acid and then sodium perborate tetrahydrate (10 equivalents) is added. The mixture is stirred at 0° C. for 2 hrs and then at ambient temperature for 2 hrs. The methanol is removed in vacuo and the residue basified with 50% sodium hydroxide solution and filtered. The filter cake is washed with methylene chloride and the aqueous filtrate extracted with the methylene chloride washings. The combined extract is washed with water, dried, and concentrated to obtain the product.

PREPARATION 13

Following the procedures of Preparation 3 and using the following reactants:
a. 4-bromo-1-[(2-bromoethyl)sulfinyl]benzene and t-butylamine.
b. 1-[(5-chloropentyl)sulfinyl]-3,4-dichlorobenzene and di-n-propylamine.
c. 1-[(4-chlorobutyl)sulfinyl]-3,4-dimethylbenzene and dimethylamine.
d. 1-[(6-chlorohexyl)sulfinyl]-2-nitro-4-trifluoromethylbenzene and diethylamine.

e. 4-acetylamino-1-[(4-chlorobutyl)sulfinyl]benzene and pyrrolidine.
f. 1-[(3-bromo-2-methylpropyl)sulfinyl]-4-nitrobenzene and dimethylamine.

there is obtained respectively:
a. N-(1,1-dimethylethyl)-2-[(4-bromophenyl)sulfinyl]-1-ethanamine.
b. N,N-di-n-propyl-5-[(3,4-dichlorophenyl)sulfinyl]-1-pentanamine.
c. N,N-dimethyl-4-[(3,4-dimethylphenyl)sulfinyl]-butanamine.
d. N,N-diethyl-6-[(2-nitro-4-trifluoromethylphenyl)sulfinyl]hexanamine.
e. N-[4-[3-(1-pyrrolidinyl)propyl]sulfinyl]phenylacetamide.
f. N,N-dimethyl-2-methyl-3-[(4-nitrophenyl)sulfinyl]-propanamine.

EXAMPLE 1

N,N-Diethyl-3-[S-(4-nitrophenyl)sulfonimidoyl]-1-propanamine dihydrochloride

Concentrated sulfuric acid (13 mL) was added dropwise to a stirring slurry of N,N-diethyl-3-[(4-nitrophenyl)sulfinyl]-1-propanamine (3.7 g, 13 mmol) and sodium azide (3.4 g, 52 mmol) in chloroform (52 mL) at −20° C. After the addition was complete, the reaction mixture was allowed to warm to ambient temperature and then warmed at reflux for 36 h. The reaction mixture was cooled to 0° C. Water (100 mL) was added, and the resulting mixture was made basic by the careful addition of 50% aqueous sodium hydroxide. The resulting layers were separated, and the aqueous layer was extracted with methylene chloride (2×50 mL). The combined organic layers were dried (MgSO$_4$) and concentrated in vacuo. Analysis ($^1$H NMR) of the residue (3.2 g) showed a 85:15 mixture of product and starting material. Careful chromatography (flash, SiO$_2$, 95:5 methylene chloride/methanol) afforded 1.5 g (38%) of the product. A 0.5 g sample of the sulfoximine was dissolved in ether and was treated with ethereal HCl. The solid that formed was collected by filtration to afford 0.6 g (96%) of white solid, mp 139°–140° C.

Analysis: Calc. for C$_{13}$H$_{21}$N$_3$O$_3$S.2HCl: C, 41.94; H, 6.23; N, 11.29; Found: C, 41.83; H, 6.47; N, 11.10.

EXAMPLE 2

S-[3-(Diethylamino)propyl]-S-(4-nitrophenyl)-N-[(phenylmethoxycarbonyl]sulfoximine monohydrochloride A slurry of N,N-diethyl-3-[S-(4-nitrophenyl)sulfonimidoyl]-1-propanamine (3.20 g, 10.7 mmol), benzyl chloroformate (2.19 g, 12.8 mmol) and potassium carbonate (4.40 g, 32.1 mmol) in methylene chloride (100 mL) was stirred at ambient temperature for 5 h. The reaction mixture was filtered, and the filtrate was concentrated in vacuo. The residue was chromatographed (Chromatatron®, 4000 μm SiO$_2$, 95:5 CH$_2$Cl$_2$/MeOH) to give 2.20 g of product (47.4%). A 0.2 g sample was dissolved in ether and treated with ethereal HCl. The white solid that formed was collected by filtration to obtain 0.15 g (67%), mp 120°–122° C.

Analysis: Calculated for C$_{21}$H$_{27}$N$_3$O$_5$S.HCl: C, 53.67; H, 6.00; N, 8.94; Found: C, 53.60; H, 6.18; N, 9.0.

EXAMPLE 3

S-[3-(Diethylamino)propyl]-S-[4-(hydroxyamino)-phenyl]-N-[(phenylmethoxy)carbonyl]sulfoximine ethanedioate (1:1)

A slurry of S-[3-(diethylamino)propyl]-S-[4-(nitrophenyl)-N-[(phenylmethoxy)carbonyl]sulfoximine hydrochloride (13.5 g, 32.3 mmol) and palladium on carbon (5% Pd/C, 0.5 g) in ethanol (150 mL) was hydrogenated on the Parr apparatus until the rapid uptake of H$_2$ stopped. The reaction mixture was filtered through a pad of Celite. The filtrate was concentrated in vacuo to give 12.4 g of the crude hydroxylamine. A 0.5 g sample was dissolved in ethyl acetate and treated with a solution of oxalic acid (0.5 g, 5 mmol) in ethyl acetate. The solid that formed was collected by filtration and recrystallized from ethanol to give 0.31 g (46%) of white solid, mp 148.5°–149.5° C.

Analysis: Calculated for C$_{21}$H$_{29}$N$_3$O$_4$S.C$_2$H$_2$O$_4$: C, 54.21; H, 6.13; N, 8.24; Found: C, 54.28; H, 6.26; N, 8.08.

EXAMPLE 4

4-[S-[3-(Diethylamino)propyl]-N-[(phenylmethoxy)carbonyl]sulfonimidoyl]benzenamine dihydrochloride A solution of S-[3-(diethylamino)propyl]-S-(4-nitrophenyl)-N-[(phenylmethoxy)carbonyl]sulfoximine (4.4 g, 11 mmol) in ethanol (100 mL) was added to a Parr hydrogenation bottle. Catalyst (Pt/C 5%, 0.5 g) was added, and the reaction mixture was hydrogenated at ambient temperature for 18 h. The reaction mixture was filtered through a pad of Celite and concentrated in vacuo. The residue (4.3 g, 6:4 mixture of hydroxylamine/product by NMR) was dissolved in ethanol (100 mL) added to a Parr hydrogenation bottle. Catalyst was added (5% Pd/C, 0.5 g), and the reaction mixture was hydrogenated at ambient temperature. The reaction mixture was filtered and concentrated in vacuo to give 3.9 g of residue (2:1 mixture of product and hydroxylamine by NMR). This residue was dissolved in ethanol (100 mL) and added to a Parr hydrogenation bottle. Catalyst (5% Pd/C, 0.5 g) was added, and the reaction mixture was hydrogenated at ambient temperature for 6 h. The reaction mixture was filtered through a pad of Celite and concentrated in vacuo to give 3.2 g (75%) on the desired amine. A 0.3 g sample was dissolved in ethanol and treated with ethereal HCl. The solid that formed was recrystallized from ethanol to give 0.28 g (64% overall) of white solid, mp 60°–64° C.

Analysis: Calculated for C$_{21}$H$_{29}$N$_3$O$_5$S.2HCl: C, 52.94; H, 6.56; N, 8.82; Found: C, 52.94; H, 6.83; N, 8.56.

EXAMPLE 5

N-[4-[S-[3-(Diethylamino)propyl]-N-[(phenylmethoxy)carbonyl]sulfonimidoyl]phenyl]methanesulfonamide hydrochloride hydrate (1:1:1)

A solution of a 3:1 mixture of 4-[S-[3-(diethylamino)-propyl]-N-[(phenylmethoxy)carbonyl]sulfonimidoyl]-benzeneamine and S-[3-(diethylamino)propyl]-S-[4-(hydroxyamino)phenyl]-N-[(phenylmethoxy)carbonyl]sulfoximine obtained through an incomplete reduction of S-[3-(diethylamino)propyl]-S-(4-nitrophenyl)-N-[(phenylmethoxy)carbonyl]sulfoximine (4.2 g, ~10 mmol) was dissolved in a pyridine (42 mL)-methylene chloride (12 mL) mixture. The resulting solution was cooled in an ice/water bath, and methanesulfonyl chloride (1.2 g, 10 mmol) was added. The reaction mixture was allowed to come to ambient temperature and was stirred for 4 h. The reaction mixture was then added to 200 mL of diethyl ether. The ethereal solution was decanted from the insoluble residue. The residue was triturated with an additional 100 mL of diethyl ether, and the ethereal solution was decanted and discarded. The residue was dried in vacuo to give 3.0 g of a gum that was chromatographed (flash, silica gel, 95:5—90:10 methylene chloride-methanol) to give 0.7 g of product (15%). A 200 mg sample was dissolved in ethanol and treated with ethereal HCl. The solid that formed was recrystallized from ethanol. This solid was triturated with ethyl acetate and then recrystallized from ethanol. The resulting solid was recrystallized from an ethanol/diethyl ether mixture to give 0.02 g of off-white solid, mp 76°-78° C.

Analysis: Calc. for $C_{22}H_{31}N_2O_3S_2 \cdot HCl \cdot H_2O$: C, 49.27; H, 6.39; N, 7.84; Found: C, 49.63; H, 6.23; N, 7.84.

EXAMPLE 6

N-[4-[S-[3-(Diethylamino)propyl]sulfonimidoyl]phenyl]methanesulfonamide hydrochloride hydrate compound with dichloromethane (2:4:3:1)

A solution of N-[4-[S-[3-(diethylamino)propyl]-N-[(phenylmethoxy)carbonyl]sulfonimidoyl]phenyl methanesulfonamide (0.40 g, 0.83 mmol) was dissolved in ethanol (100 mL) and added to a Parr hydrogenation bottle. Catalyst (10% Pd/C, 0.5 g) was added, and the reaction mixture was hydrogenated at ambient temperature for 1 h and at 35° C. for 4 h. The reaction mixture was then hydrogenated at ambient temperature overnight. The reaction mixture was filtered and concentrated in vacuo. The residue was dissolved in ethanol (20 mL) and treated with ethereal HCl. A semi-solid formed, and the remaining solution was decanted. The semi-solid was triturated with ether to give a solid, which was collected by filtration and dried in vacuo. This sample was dissolved in water (10 mL), and the aqueous solution was washed with ether (3×10 mL) and methylene chloride (10 mL). The aqueous layer was concentrated in vacuo (repeated twice). The resulting foam was triturated with methylene chloride. The methylene chloride solution was decanted, and the resulting solid was dried in vacuo to obtain a white solid (0.09 g, 22%), mp 64°-67° C.

Analysis: Calculated for $C_{14}H_{25}N_3O_3S_2 \cdot 2HCl \cdot 0.5CH_2Cl_2 \cdot 1.5H_2O$: C, 35.55; H, 6.38; N, 8.58; Found: C, 35.83; H, 6.03; N, 8.66.

EXAMPLE 7

N,N-Diethyl-N-methyl-3-[S-(4-nitrophenyl)sulfonimidoyl]propanaminium tetrafluoroborate Trimethyloxonium fluoroborate (3.81 g, 25.6 mmol) was added to a solution of N,N-diethyl-3-[S-(4-nitrophenyl)sulfonimidoyl]-1-propanamine (7.7 g, 25.6 mmol) in methylene chloride (50 mL) maintained at −20° C. After 15 min the reaction mixture was warmed to 0° C. for 30 min and then to ambient temperature for 1 h. Water (100 mL) was added to the reaction mixture, and the reaction mixture was made basic with 10% sodium hydroxide. The biphasic mixture containing insoluble material was filtered. The solid that was collected by filtration was recrystallized from a methanol/ethanol mixture. The white solid that formed was collected by filtration to give 0.51 g(4.9%), mp 125°-126.5° C.

Analysis: Calc. for $C_{14}H_{24}N_3O_3S \cdot BF_4$: C, 41.91; H, 6.03; N, 10.47; Found: C, 41.91; H, 6.14; N, 10.25.

EXAMPLE 8

N,N-Diethyl-3-[N-(methylsulfonyl)-S-(4-nitrophenyl)-sulfonimidoyl]-1-propanamine ethanol (2:1)

N,N-Diethyl-3-[S-(4-nitrophenyl)sulfoximidoyl]-1-propanamine (2.59 g, 8.66 mmol) was dissolved in methylene chloride (50 mL) and methanesulfonic anhydride (1.66 g, 9.52 mmol) was added. After stirring for 3 h at ambient temperature, a solution of 2.5% aqueous sodium hydroxide (100 mL) was added. The layers were separated, and the organic layer was washed with water (100 mL). The organic layer was dried (MgSO₄) and concentrated in vacuo. The residue was chromatographed in 2 batches (Chromatatron, 4000μ, SiO₂, 98:2—9:1 methylene chloride-methanol). The appropriate fractions of the first batch were concentrated, and the residue was dissolved in diethyl ether. The ethereal solution was treated with ethereal HCl, and the white solid that formed was collected by filtration (1.31 g, 35%), mp 62°-65° C.

Analysis: Calc. for $C_{14}H_{23}N_3O_5S_2 \cdot 0.5C_2H_6O$: C, 41.23; H, 6.23; N, 9.62; Found: C, 41.37; H, 6.50; N, 9.40.

EXAMPLE 9

Following the procedures of Example 1 and using the following sulfinyl intermediates:

a. N-(1,1-dimethylethyl)-2-[(4-bromophenyl)sulfinyl]ethanamine
b. N,N-di-n-propyl-5-[(3,4-dichlorophenyl)sulfinyl]pentanamine
c. N,N-dimethyl-4-[(3,4-dimethylphenyl)sulfinyl]butanamine
d. N,N-diethyl-6-[(2-nitro-4-trifluoromethylphenyl)sulfinyl]hexanamine
e. N-[4-[3-(1-pyrrolidinyl)propyl]sulfinyl]phenyl acetamide
f. N,N-dimethyl-2-methyl-3-[(4-nitrophenyl)sulfinyl]propanamine
g. 1-[[2-(4-morpholinyl)ethyl]sulfinyl]-4-nitrobenzene there is obtained respectively:
a. S-[2-[(1,1-dimethylethyl)amino]ethyl]-S-(4-bromophenyl)sulfoximine.
b. S-[5-(dipropylamino)pentyl]-S-(3,4-dichlorophenyl)sulfoximine.
c. S-[4-(N,N-dimethylamino)butyl]-S-(3,4-dimethylphenyl)sulfoximine
d. S-[6-(diethylamino)hexyl]-S-(2-nitro-4-trifluoromethylphenyl)sulfoximine
e. S-(4-acetylaminophenyl)-S-[3-(1-pyrrolidinyl)propyl]sulfoximine
f. S-[3-(N,N-dimethyl-2-methyl)propyl]-S-3-(4-nitrophenyl)sulfoximine
g. S-[2-(4-morpholinyl)ethyl]-S-(4-nitrophenyl)sulfoximine.

EXAMPLE 10

S-[5-(diethylamino)hexyl]-N-[(dimethylamino)carbonyl]-S-(2-nitro-4-trifluoromethylphenyl)sulfoximine Following the procedures of Example 2, the title compound is obtained from S-[6-(diethylamino)hexyl]-S-(2-nitro-4-trifluoromethylphenyl)sulfoximine and dimethylcarbamoyl chloride.

EXAMPLE 11

S-(3,4-dichlorophenyl)-S-[5-(dipropylamino)pentyl]-N-[(propylamino)carbonyl]sulfoximine A mixture of equimolar amounts of S-[5-(dipropylamino)pentyl]-S-(3,4-dichlorophenyl)sulfoximine and methylisocyanate are stirred together in methylene chloride to obtain the title compound.

EXAMPLE 12

N-acetyl-S-[3-(diethylamino)propyl]-S-(4-nitrophenyl)-sulfoximine

Following the procedures of Example 2, the title compound is prepared from S-[3-(diethylamino)propyl]-S-(4-nitrophenyl)sulfoximine and acetylchloride.

EXAMPLE 13

N-methyl-S-(3-diethylaminopropyl)-S-(4-nitrophenyl)-sulfoximine

A mixture of S-(3-diethylaminopropyl)-S-(4-nitrophenyl)sulfoximine (0.03 mole), 17 ml of 37% formaldehyde, and 22.6 ml of 98% formic acid is heated at reflux temperature for 48 hr. Water is added to the reaction mixture which is then made slightly basic by addition of 50% sodium hydroxide solution. The mixture is extracted with chloroform and the extract is dried and concentrated to obtain the title compound.

EXAMPLE 14

N-Ethyl-S-(3-diethylaminopropyl)-S-(4-nitrophenyl)-sulfoximine

A solution of S-(3-diethylaminopropyl)-S-(4-nitrophenyl)sulfoximine (10 mmol) in dimethylformamide is added to a stirred suspension of 60% sodium hydride-oil dispersion (10 mmol) at ambient temperature. After stirring for 30 min the mixture is warmed to 50° C. for 30 min and then cooled to ambient temperature. Iodoethane (10 mmol) is added dropwise to the reaction mixture and stirred at ambient temperature for 30 min and then warmed to 50° C. for 1 hr. The reaction mixture is diluted with water and extracted with methylene chloride. The methylene chloride extract is concentrated in vacuo and the residue partitioned between methylene chloride-1N hydrochloric acid. The acid layer is separated and basified with 50% sodium hydroxide solution and extracted with methylene chloride. The methylene chloride extract is washed with water, dried, and concentrated to obtain the title compound.

EXAMPLE 15

N-Benzyl-S-(3-diethylaminopropyl)-S-(4-nitrophenyl)-sulfoximine

Following the procedures of Example 14 and substituting benzyl bromide for iodoethane, the title compound is obtained.

TABLE 1

| Example | $X^1$ | $X^2$ | Y | Z | $NR^1R^2$ |
|---|---|---|---|---|---|
| 1 | $NO_2$ | H | H | $(CH_2)_3-$ | $NEt_2$ |
| 2 | $NO_2$ | H | $-\overset{O}{\underset{\|}{C}}OCH_2C_6H_5$ | $-(CH_2)_3-$ | $NEt_2$ |
| 3 | HONH | H | $-\overset{O}{\underset{\|}{C}}OCH_2C_6H_5$ | $-(CH_2)_3-$ | $NEt_2$ |
| 4 | $H_2N$ | H | $-\overset{O}{\underset{\|}{C}}OCH_2C_6H_5$ | $-(CH_2)_3-$ | $NEt_2$ |
| 5 | $CH_3SO_2NH$ | H | $-\overset{O}{\underset{\|}{C}}OCH_2C_6H_5$ | $-(CH_2)_3-$ | $NEt_2$ |
| 6 | $CH_3SO_2NH$ | H | H | $-(CH_2)_3-$ | $NEt_2$ |
| 7 | $O_2N$ | H | H | $-(CH_2)_3-$ | $N^{\oplus}(Et_2)CH_3BF_4^{\ominus}$ |
| 8 | $O_2N$ | H | $SO_2CH_3$ | $-(CH_2)_3-$ | $NEt_2$ |
| 9a | Br | H | H | $-(CH_2)_2-$ | NH-t-butyl |
| 9b | Cl | 3-Cl | H | $-(CH_2)_5-$ | $NPr_2$ |
| 9c | $CH_3$ | 3-$CH_3$ | H | $-(CH_2)_4-$ | $NMe_2$ |
| 9d | $CF_3$ | 2-$NO_2$ | H | $-(CH_2)_6-$ | $NEt_2$ |
| 9e | $\overset{O}{\underset{\|}{CH_3CNH}}$ | H | H | $-(CH_2)_3-$ | (azepane ring) |
| 9f | $O_2N$ | H | H | $-CH_2\underset{CH_3}{\overset{\|}{CH}}CH_2-$ | $NMe_2$ |

TABLE 1-continued $$X^1 \text{—} \underset{X^2}{\underset{|}{\bigcirc}} \text{—} \underset{\underset{N}{\overset{O}{\|}}}{\overset{O}{\underset{\|}{S}}} \text{—} Z \text{—} N \overset{R^1}{\underset{R^2}{\diagdown}}$$

| Example | X¹ | X² | Y | Z | NR¹R² |
|---|---|---|---|---|---|
| 9g | O₂N | H | H | —(CH₂)₂— | ⟨N O⟩ (morpholino) |
| 10 | CF₃ | 2-NO₂ | O‖ —CNME₂ | —(CH₂)₆— | NEt₂ |
| 11 | Cl | 3-Cl | O‖ —CNHCH₃ | —(CH₂)₅— | NPr₂ |
| 12 | O₂N | H | O‖ —CCH₃ | —(CH₂)₃— | NEt₂ |
| 13 | O₂N | H | —CH₃ | —(CH₂)₃— | NEt₂ |
| 14 | O₂N | H | —CH₂CH₃ | —(CH₂)₃— | NEt₂ |
| 15 | O₂N | H | —CH₂C₆H₅ | —(CH₂)₃— | NEt₂ |

Pharmacology and Pharmaceutical Compositions

Measurement of Cellular Electrophysiologic Effects in Canine Purkinje Fibers in Vitro Dogs (12-18 Kg) were anesthetized with sodium pentobarbital (30 mg/kg IV). The heart of each dog was rapidly removed through a right lateral thoracotomy and placed in a chilled, oxygenated Tyrode's solution. Purkinje fibers from the right and left ventricles were excised and mounted in a Lucite chamber. The tissue was superfused at a rate of 10-15 ml/min with Tyrode's solution. The temperature of the superfused Tyrode's was maintained at 37° C. and gassed with 95% oxygen-5% carbon dioxide mixture.

The Purkinje fibers were stimulated (paced at cycle length of 400 to 1000 msec) with a silver bipolar wire electrode placed on the surface of the tissue. Transmembrane action potentials were recorded with a glass capillary microelectrodes filled with 3M KCl. The action potentials were displayed on a Tectronix 5113 oscilloscope. The measurements derived from the action potential were Vmax (upstroke velocity), APD50 (action potential duration at 50% repolarization), and APD90 (action potential duration at 90% repolarization) as previously described (Bigger and Mandel, 1970; Wu and Hoffman, 1987). Test compounds were added to the reservoir of Tyrode's solution to concentrations of 10 and 100 μm. Measurements of the action potential parameters were recorded after 20 min of test drug exposure. These measurements were compared to those obtained prior to the test compound. Changes in the action potential measurements produced by the test compound were analyzed for statistical significance using a paired-t test. A minimum of 3 tissues were used for each test compound.

Bigger JT and Mandel WJ. Effects of lidocaine on the electrophysiologic properties of ventricular muscle and Purkinje fibers. J. CLIN. INVEST. Vol. 49:63-77 (1970).

Wu KM and Hoffman BF. Effect of procainamide and N-acetylprocainamide on atrial flutter; studies in vivo and in vitro. CIRCULATION Vol. 76:1397-1408 (1987).

TABLE 2

| | Pharmacology Data | |
|---|---|---|
| Ex. | Conc (M) | APD 90 % change | ADP 50 % change |
| 1 | 10⁻⁵ | 20.9 ± 7.1* | 19.3 ± 8.9* |
| | 10⁻⁴ | 50.5 ± 14.3* | 48.8 ± 13.4* |
| 2 | 10⁻⁵ | 11.4 ± 11.1* | 2.1 ± 10.5 |
| | 10⁻⁴ | 15.1 ± 9.6* | 9.3 ± 12.3 |
| 6 | 10⁻⁵ | 4.8 ± 3.1* | 3.0 ± 3.8 |
| | 10⁻⁴ | 17.9 ± 11.1* | 23.8 ± 13.6* |
| 8 | 10⁻⁵ | 11.8 ± 4.6* | 10.1 ± 5.6 |
| | 10⁻⁴ | 12.9 ± 2.7 | 3.8 ± 9.1 |

* = significant change from controls.

Generally, the method of treating cardiac arrhythmia in accordance with this invention comprises administering internally to warm-blooded animals, including human beings, a therapeutically effective amount of a compound of Formula I or a pharmaceutically acceptable salt in a wide variety of pharmaceutical forms well known in the art, preferably with a non-toxic pharmaceutical carrier. The active agent is administered orally, subcutaneously, intravenously, or intramuscularly and, if necessary, in repeated dosages until satisfactory response is obtained. Compositions for oral administration can take the form of elixirs, capsules, tablets, or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone. For parenteral administration, the carrier or excipient can be comprised of a sterile parenterally acceptable liquid, e.g., water or arachis oil contained in ampoules.

The effective antiarrhythmic dose of a Formula I compound in warm-blooded animals is expected to be in the range of from 0.01 to 100 mg/kg and will further depend on the compound used and the route of administration.

It is only necessary that a suitable effective dosage be consistent with the dosage form employed. The exact individual dosages, as well as the daily dosages, will of course be determined according to standard medical principles under the direction of a physician or veterinarian.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention, and it is therefore understood that the invention is to be limited only by the scope of the appended claims.

What is claimed is:

1. A compound according to the formula

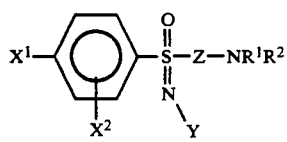

Formula I wherein:
X$^1$ is —NO$_2$;
X$^2$ is hydrogen;
Y is H;
Z is C$_2$-C$_6$ alkylene;
R$^1$ and R$^2$ are H or C$_1$-C$_6$ alkyl; [R$^3$ is hydrogen, C$_1$-C$_6$ alkyl, benzyl] or a pharmaceutically acceptable salt thereof.

2. A compound according to claim 1 which is selected from
N,N-diethyl-3-[S-(4-nitrophenyl)sulfonimidoyl]-1-propanamine, and
N,N-diethyl-N-methyl-3-[S-(4-nitrophenyl)sulfonimidoyl]propanium tetrafluoroborate[, and
N,N-diethyl-3-[N-(methylsulfonyl)-S-(4-nitrophenyl)sulfonimidoyl]-1-propanamine].

3. A method of treating certain cardiac arrhythmias by internally administering to a warm blooded animal a therapeutically effective amount of a compound according to:

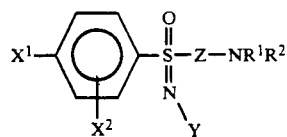

Formula I wherein:
X$^1$ is —NO$_2$;
X$^2$ is hydrogen;
Y is H;
Z is C$_2$-C$_6$ alkylene;
R$^1$ and R$^2$ are H or C$_1$-C$_6$ or a pharmaceutically acceptable salt thereof.

4. A method of treating certain cardiac arrhythmias by internally administering to a warm-blooded animal a therapeutically effective amount of a compound selected from:
N,N-diethyl-3-[S-(4-nitrophenyl)sulfonimidoyl]-1-propanamine, and
N,N-diethyl-N-methyl-3-[S-(4-nitrophenyl)sulfonimidoyl]propanium tetrafluoroborate.

5. A pharmaceutical composition for the treatment of certain cardiac arrhythmias in warm-blooded animals comprised of:
a. a therapeutically effective amount of a compound according to the formula:

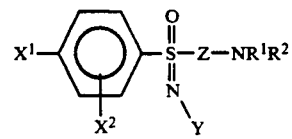

Formula I wherein:
X$^1$ is —NO$_2$;
X$^2$ is hydrogen;
Y is H;
Z is C$_2$-C$_6$ alkylene;
R$^1$ and R$^2$ are H or C$_1$-C$_6$ alkyl; [R$^3$ is hydrogen, C$_1$-C$_6$ alkyl, benzyl] or a pharmaceutically acceptable salt thereof, and
b. a pharmaceutical carrier thereof.

* * * * *